United States Patent [19]

Schmid-Schönbein et al.

[11] 4,352,557
[45] Oct. 5, 1982

[54] DETERMINING A TEST VALUE CORRESPONDING TO BLOOD SUBSIDENCE

[75] Inventors: Holger Schmid-Schönbein; Holger Kiesewetter; Klaus Mussler, all of Aachen; Heinz Myrenne, Roetgen; Andreas Scheffler, Wuppertal, all of Fed. Rep. of Germany

[73] Assignee: Ernst Leitz Wetzlar GmbH, Wetzlar, Fed. Rep. of Germany

[21] Appl. No.: 141,638

[22] Filed: Apr. 18, 1980

[30] Foreign Application Priority Data

Oct. 20, 1979 [DE] Fed. Rep. of Germany ....... 2942466
Mar. 11, 1980 [DE] Fed. Rep. of Germany ....... 3009260

[51] Int. Cl.³ ............................................. G01N 33/48
[52] U.S. Cl. ....................................... 356/39; 356/40; 356/427
[58] Field of Search ........................... 356/39, 40, 427; 250/556

[56] References Cited

U.S. PATENT DOCUMENTS 3,706,877 12/1972 Clifford, Jr. et al. ............... 250/556
4,135,819 1/1979 Schmid-Schönbein ............... 356/39
4,252,536 2/1981 Kishimoto et al. .................... 356/39

OTHER PUBLICATIONS

Quantitative Evaluation of the Rate of Rouleaux Formation of Erythrocytes by Measuring Light Reflection ("Syllectometry"), Brinkman et al., Reprinted From Proceedings Series C, 66, No. 3, 1963.
"Microheology & Protein Chemistry of Pathological Red Cell Aggregation (Blood Sludge) Studied in Vitro", Schmid–Schönbein et al., Biorhcology, 1973, vol. 10, pp. 213-227.
Brinkman, Zijlstra & Jansonius, "Syllectometry", Nov. 3, 1963, Koninkl. Nederl. Akademie, C. 66, pp. 236-248.
Schmid–Schönbein et al., "Rheoscope Chamber", Microvascular Research, vol. 6, pp. 366-376, (1973).
Schmid–Schönbein et al., "New Hemorheological Techniques etc.", Recent Advances in Cardiovascular Disease, vol. II, Supp. Aug. 1981, pp. 27-39.

Primary Examiner—Vincent P. McGraw
Attorney, Agent, or Firm—Wells & Wells

[57] ABSTRACT

A test value corresponding to blood subsidence from a syllectogram is determined as a result of the effect of shearing forces on a blood sample, by ascertaining the slope of the test curve representing the syllectogram at a predetermined time beginning with or after the onset of the blood aggregation phase as the test value after:
(a) sudden stoppage of the shearing; or
(b) a transition to a continuous minor residual shearing.

12 Claims, 7 Drawing Figures

DETERMINING A TEST VALUE CORRESPONDING TO BLOOD SUBSIDENCE

CROSS-REFERENCE TO RELATED APPLICATIONS

Applicants claim priority under 35 USC 119 for application Ser. No. P 29 42 466. 6, filed Oct. 20, 1979 and for Ser. No. 30 09 260.5 filed Mar. 11, 1980 in the Patent Office of the Federal Republic of Germany.

BACKGROUND OF THE INVENTION

The field of the invention is blood analysis by optics, measuring and testing and the invention is particularly related to a method and apparatus for determining a test value corresponding to blood subsidence from a syllectogram of a blood sample that is being subjected to shear forces.

The state of the art of determining a test value corresponding to blood subsidence from a syllectogram of a blood sample that was or is being subjected to shear forces may be ascertained by reference to the article entitled "Syllectometry" by Zijlstra, as published in the Proc. Koninkl. Nederl. Akad. v. Wetensch., Amsterdam, Ser. C., Vol. 66, no. 3 (1963) at pp. 237–248.; Microvascular Research, Vol. 6, (1973), pp. 366–376; and U.S. Pat. No. 4,135,819, of Schmid-Schönbein, the disclosures of which are incorporated herein.

U.S. Pat. No. 4,135,819 discloses an apparatus and method for measuring the aggregation rate of capillary native blood free of coagulation inhibitor in order to quickly ascertain information disclosing blood subsidence from a minimum amount of blood. In U.S. Pat. No. 4,135,819, the light transmission of a blood sample is recorded as a function of time. This magnitude changes as a function of the significant rheological phenomenon, the erythrocyte aggregation, and therefore permits data to be obtained. Photometric aggregometry may be measured both in transmission and reflection. The test curve obtained was first coined "syllectogram" by Zijlstra, op. cit. It is based on the fact that the scattering of light in a blood sample decreases after aggregates are formed and the transmission of light increases accordingly.

Three basic phases must be distinguished in the course of a measurement, namely: (1) the mixing phase, (2) the stopping phase, i.e., the phase of slight shearing, and (3) the aggregation phase. To carry out the measurement, a blood sample is introduced into a measuring chamber consisting essentially of a transparent, disk-cone system rotating in the same or mutually opposite directions. During the mixing phase, the erythrocytes orient themselves under the influence of shearing forces and thus create clear plasma spaces by means of which the light can pass through the blood sample. In view of the material inhomogeneities in the path of the light beam, the light transmission fluctuates about a mean value.

When the shearing is terminated by abruptly stopping the disk-cone system, there is an impulsive disorientation of the blood cells and as a consequence of the elimination of clear plasma spaces, there is also a reduction in the transmission.

With the ensuing onset of aggregation, the number of plasma gaps grows again and therefore the transmission increases again. The change of this transmission with time is essentially exponential.

This time curve is quite reproducible, so that first the half-value time characteristic of an exponential function was determined to be the numerical value. It has been found, however, that no unambiguous correlation could be obtained between this numerical value and the conventionally obtained blood subsidence values.

It is furthermore known from Microvascular Research, op. cit., that the syllectogram representing the time function of erythrocyte aggregation presents a significantly higher test value in the presence of a slight residual shearing than for the measurement at rest.

U.S. Pat. No. 4,135,819 proposed not to use the measured curve, but its derivative with time. This differentiated curve is also exponential, whereby the erythrocyte aggregation again can be represented by the half-value time of the differentiated syllectogram. The half-value time is plotted by hand, or for a rapid aggregation by electronic differentiation. But it has been found that while the analog differentiation is quite suitable for all pathological, i.e., rapid aggregation processes, it requires a high expenditure in material for the slow ones. This is especially the case for extremely decelerated aggregation which occurs in healthy blood after it is diluted by an anticoagulant dissolved therein.

SUMMARY OF THE INVENTION

Having in mind the limitations of the prior art, it is an object of the present invention to analyze the syllectogram in a manner independent of the function of time of the erythrocyte aggregation and by a quick and simple way of measuring which can be visually displayed as regards the rate of blood subsidence which is being sought.

This object is achieved according to the present invention either after a sudden stoppage of shearing or after a transition to a continuous minor residual shearing. A test value is taken which is the slope of the syllectogram at a predetermined instant after the onset of the aggregation phase. This time is appropriately set at 2.5 seconds after onset of the aggregation phase. To decrease the influence of accidental interference, advantageously the test value is the mean slope of the syllectogram rather than a single slope within a predetermined time interval from onset of the aggregation phase. Again, this time interval selected is 2.5 seconds.

An alternative method is to determine the area under the syllectogram within a predetermined time interval beginning with the onset of the aggregation phase as the test value. This time interval amounts to about 10 seconds. The onset of the aggregation phase is determined by ascertaining an extreme value of the syllectogram within a predetermined time interval following stopping of the shearing or transition to a continuous minor residual shearing. This time interval is selected to be 5 seconds.

The transition to a continuous minor residual shearing takes place in mathematically continuous or discontinuous manner.

BRIEF DESCRIPTION OF THE DRAWINGS

The apparatus used in the present invention may best be explained by reference to the appended drawings, wherein.

DESCRIPTION OF THE DRAWINGS

Figures 1, 1A, 1B:
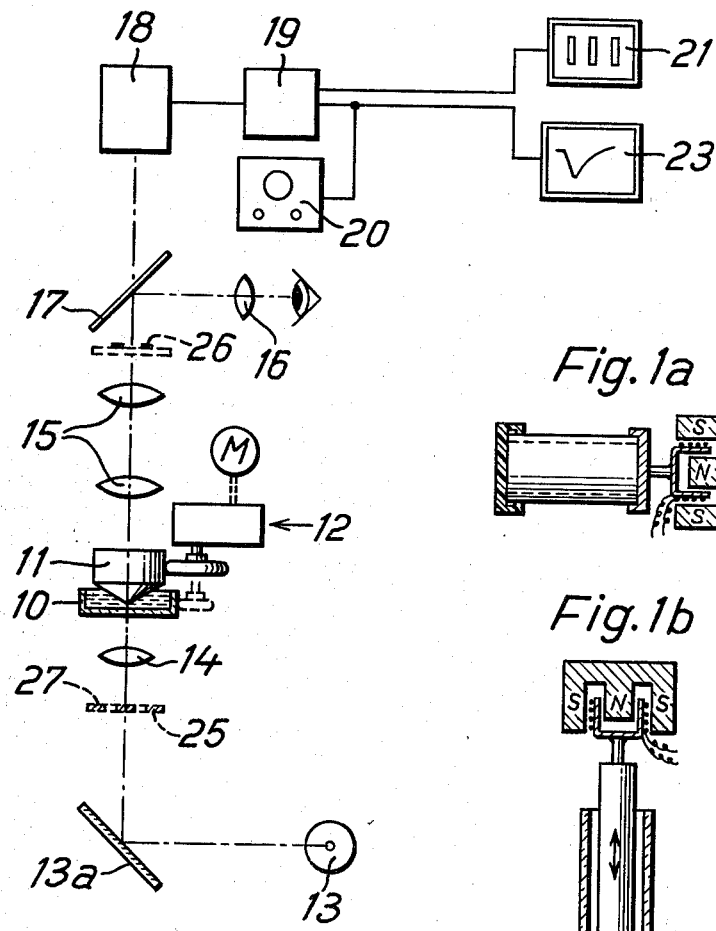
FIG. 1 is a plan view of an embodiment of the apparatus used in the present invention shown in diagrammatic form.
FIGS. 1a and 1b show other embodiments for the mixing tub.
Figure 2:
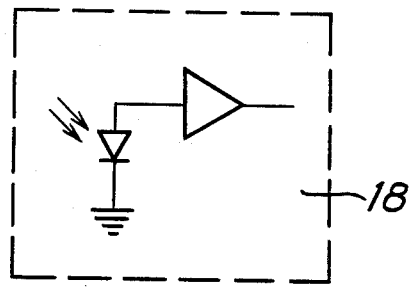
FIG. 2 is a detailed showing of an embodiment for the photoelectric system 18 of FIG. 1.
Figure 4:
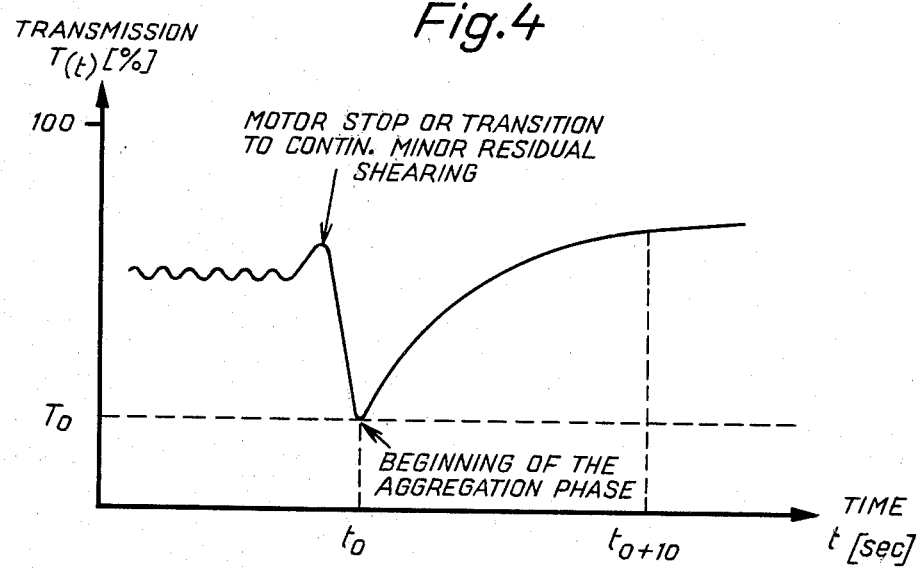
FIG. 4 is a plot showing a test curve representing a syllectogram after sudden stoppage of the shearing or after a transition to a continuous minor residual shearing.
Figure 5:
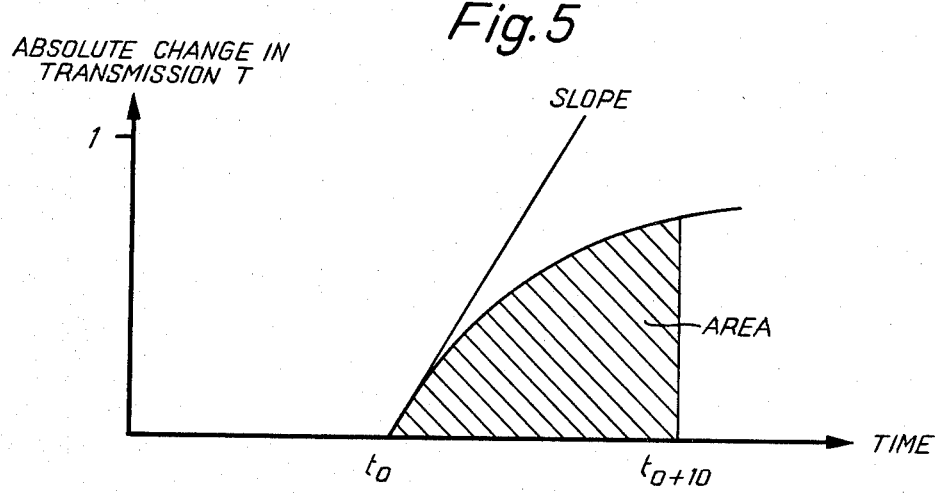
FIG. 5 is a plot showing the slope of a test curve representing a syllectogram and the area under the test curve.
Figure 3:
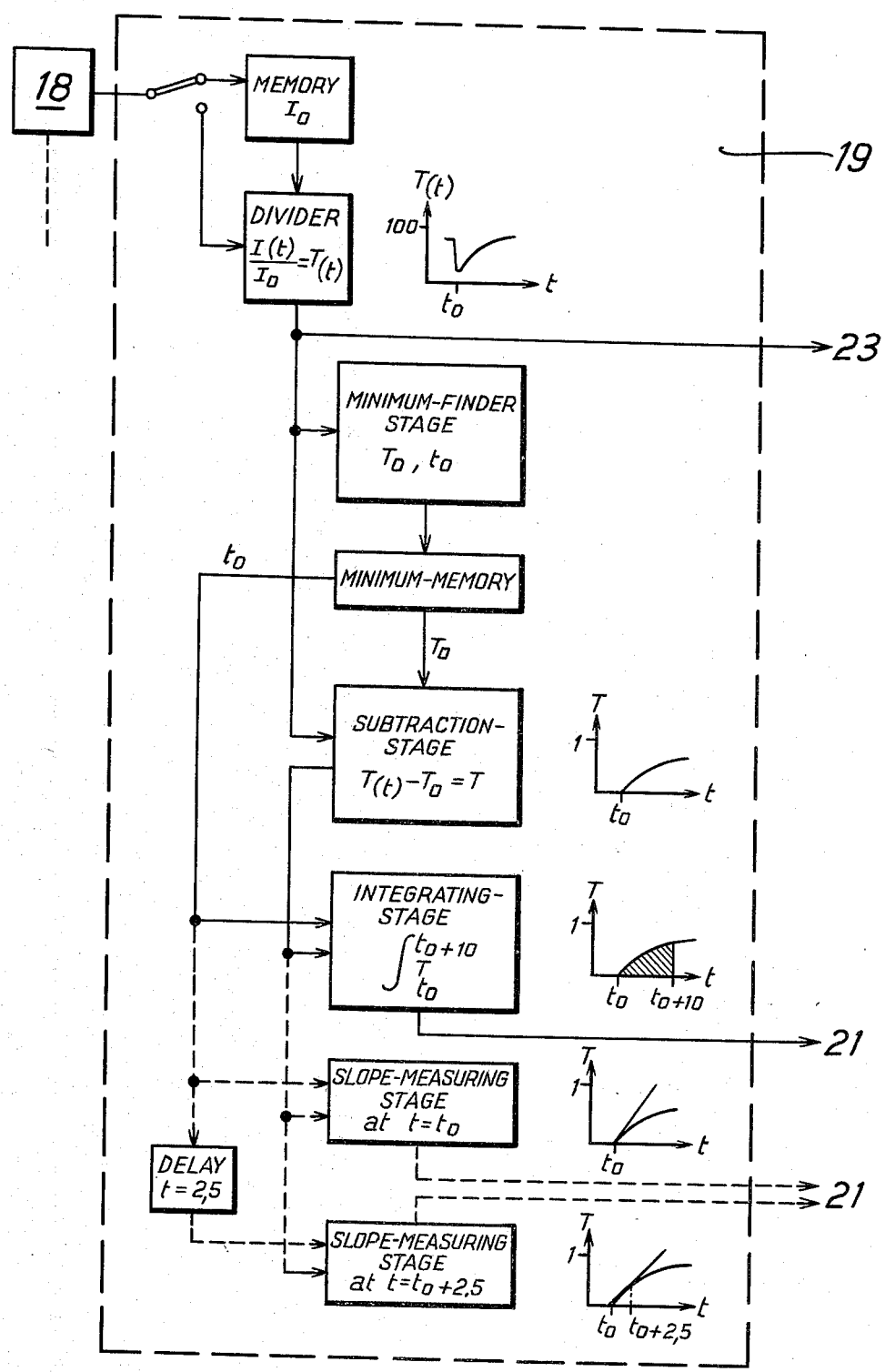
FIG. 3 is a detailed showing of an embodiment for the analyzing stage 19 of FIG. 1.

As shown in FIG. 1, the apparatus comprises a mixing chamber in the design of a tub 10 receiving the blood to be tested. A cone 11 pivotable about its axis of rotation causing the mixing process penetrates this tub. The tub and cone are made of a transparent material and so dimensioned that for a given range of rotational speeds of the cone, no significant centrifugal forces are applied to the blood being tested. A drive 12 equipped with fast shut-off actuates cone 11 which thus disperses the blood particles. Tub and cone are illuminated from a light source 13 by means of a deflecting mirror 13*a* and a condenser 14. Visual observation of the test substance is made possible by an objective 15 and a splitter 17 and an ocular 16. Splitter 17 is followed by a photoelectric system 18 which shapes as shown in FIG. 2 the light flux that comes from the tub, cone, objective and splitter into proportional electric signals. An analyzing stage 19 follows this system 18, ascertaining the modification of the output signals from equipment 18.

In addition to the above description, optical components (reference numerals 25, 26) are inserted along the optical axis of FIG. 1. These components on account of their special design affect the light amplitude alone of both the light amplitude and phase. As shown, the components in the given embodiment consist of a stop 25 with circular aperture 27 positioned in front of chamber 10, and of an annular structure located in a conjugate plane and adapted in its dimensions to the image of annular stop 25. When this structure for instance is a dyed-in layer, then both the amplitude and the phase of the light reaching detector 18 will be affected. When structure 26 is a neutral density filter, only the light amplitude will be affected. The two measurements are appropriate when the object to be examined predominantly affects the phase, but not the amplitude of the light. The above offers but one of many possible embodiments. Thus, tub and rotational body might also be made spherical. Again, the mixing chamber itself may be used to disperse the substance by being supported elastically and being shaken for instance by one or several piezo electric resonators or oscillators, or by a loud speaker. In such cases the chamber appropriately will be of tubular form (FIG. 1*a*). Again, one may disperse the blood inside a tubular mixing chamber by the to and fro motion of a stirrer dipping into the tube and the motion of which may be stopped abruptly (FIG. 1*b*).

When the blood being tested is put into motion by rotating the cone, existing particle aggregates dissolve. But they reform when cone rotation is stopped or retarded and hence the blood returns to rest. This causes a change in transparency and hence a change in the output signals from equipment 18. Test values may be displayed digitally at stage 21 following stage 19, or they may be stored in a memory 23. These components 21 and 23 are disclosed in U.S. Pat. Nos. 3,317,736, FIG. 3 and 3,306,095, FIG. 1. When using a warning system, the instrumentation shown may also be used for series (assembly line) tests.

DESCRIPTION OF THE PREFERRED EMBODIMENTS

As regards the further electronic processing of the syllectogram, it is especially advantageous to digitize the test curve. Good resolution is achieved if digitizing takes place at a frequency of 20 Hz.

To carry out control measurements, the digitized test values appropriately are multiplied by a factor normalizing the incident light intensity. Information about the absolute, aggregation-determined change in light intensity is obtained when the digitized syllectogram is normalized within the predetermined testing time interval by subtracting the test value defining the onset of the aggregation phase. In a preferred embodiment of the present invention, the area under the normalized digitized syllectogram is determined by numerical integration during the predetermined time interval.

Improved control for interpreting the test results is obtained when measurements are carried out alternatingly for sudden stoppage after shearing and after transition to a residual shearing.

The present invention is advantageously useful also for agglutination research if a minor residual shearing is maintained during the time of measurement.

Contrary to the prior art analytical methods for the syllectogram, which must take into account the curve over a substantial length of time in order to determine the half-value time, the present invention is restricted to the curve of the first few seconds. In particular cases, the time of measurement is determined not by the particular curve, but by empirical data independent therefrom.

The actual time of measurement, which includes the stopping phase and the aggregation phase, is for instance 7.5 seconds for the slope measurement and 15 seconds for the area measurement, so that a very rapid analytical process is available for diagnostic purposes.

The present invention is based on the results from comprehensive mathematical research in the curves representing the syllectogram. By iteratively adapting to the analog curve and computing a compensating spline, it is found that the function of the change of light intensity in the aggregation phase represents a natural process only during the first seconds, this function being superposed by others in the further course of the test run.

The determination of the slope of the syllectogram at a given instant, or the mean slope for a predetermined time interval after onset of the aggregation phase is a measure of the rate of aggregation. The area under the test curve within a predetermined time interval quantifies the magnitude of the aggregation that took place. Both magnitudes measure aspects of the primary aggregation process which is also responsible for the conventional measurement of the rate of blood subsidence.

It is manifest therefore that the values found for the rate of aggregation are interpreted in the same manner as for the rate of blood subsidence. But the values for the area also provide numerical data proportional to those of the rate of blood subsidence, as the area is zero when no aggregation takes place after the stopping phase and a maximum when the aggregation is practically fully completed within the time of testing. The area is considerably smaller for healthy blood than for pathological blood, and this agrees with the rate of blood subsidence in the normalized range for wholly healthy individuals.

The variation in the above described method, wherein the stopping phase ensuing the mixing phase is replaced by a phase of minor shearing which is furthermore maintained during the following phase of aggregation, is advantageous for instance when the test chamber consists of a stator and a rotor for the disaggregation of the erythrocytes. Depending on the thickness of the sample layer, a flow gradient may develop on account of inertia within the sample after the sudden stopping of the rotor, whereby time-decreasing shearing forces are generated during the photometric test.

It is known from the earlier measurements conducted according to the prior art cited above that a minor shearing action affects the course of the (otherwise) natural erythrocyte aggregation. This effect is more pronounced in pathological blood samples than in healthy ones and is opposite to the latter. A time-varying disaggregation determined by the flow conditions therefore affects the natural aggregation in a manner which cannot be accounted for by measurement techniques.

The transition of the present invention to a continuous minor residual shearing on the other hand creates specific testing conditions because the proportion of the shear-induced aggregation then is a constant.

Advantageously also the measurements are carried out alternatingly following the stopping phase and in the shear-induced phase, as the comparison of the test results provides a further index for the presence of pathological blood samples. The effect of the shear-induced aggregation for instance is especially significant in rheumatic sufferers.

New research furthermore has shown that the agglutination of blood takes place at substantially accelerated pace when under the influence of minor shearing forces. The known cross-match tests for determining blood group incompatibility require a waiting time of about half an hour when the conventional methods are used.

On the other hand, when a syllectogram is taken in the presence of sustained shearing force, an indication is already provided after about 30 seconds. This makes it possible for the first time to ascertain blood group incompatibility during a blood transfusion and to stop the transfusion from proceeding.

BEST MODE OF CARRYING OUT THE INVENTION

An illustration of the present invention using area determination is described below in relation to a transmission syllectogram. To record the syllectogram, the photometric system described in FIGS. 1 to 3 and U.S. Pat. No. 4,135,819 is used. A micro-computer with suitable program modules is used to carry out the novel analytical procedure.

The incident light intensity must be known before a test run begins in order to carry out transmission measurements. To that end the digital input of a digital-analog converter (DAC) is increased until the measured value for the empty chamber is balanced to 100% transmission.

The reference value for the incident intensity is represented by the last value of the DAC input register and stored in the microcomputer memory.

Thereupon the test chamber is filled with the blood sample. The program starts the chamber drive to eliminate the aggregation which is present. A transmission constantly fluctuating about a mean value sets in. The end of the mixing phase is controlled in terms of a given number of revolutions of the cone-disk system of the test chamber. The end of the mixing phase is determined by a revolution counter. The chamber drive motor is stopped and the test data recording begins. The transmission data are transferred at a frequency of 20 Hz for 15 seconds following motor stoppage by an analog-digital converter (ADC) and stored in the micro-computer memory. The reference value obtained for the incident light intensity is kept constant through a testing cycle, and the transmission data are referred to it.

Analysis begins with the determination of the start $(T_o, t_o)$ of aggregation. This is defined as the absolute minimum of the transmission curve $\pi(t)$ within the first 5 seconds after motor stoppage.

By subtracting the transmission $T_o$ measured at the onset of the aggregation from all subsequent measured values in the time interval $(t_o, t_o+10)$, the curve of the absolute changes in transmission, referred to the initial value, caused by the progressive aggregation of the erythrocytes, is obtained.

The transmission changes so computed can be used in a so-called quadrant correlation test by Quenouille to determine whether measurable aggregation took place at all in the tested blood sample, because, as already mentioned, the aggregation may be null in healthy subjects. If there is no aggregation, there is consequently no integration of changes in transmission, rather the result is indicated immediately.

The numerical integration of the computed changes in transmission can be implemented by successively summing segments of area by means of an algorithm fitted to the test procedure. Advantageously, a compensating parabola is computed by means of 5 particular successive measuring points with subscripts $i_n - i_{n+4}$ corresponding to a time interval of 0.2 seconds, this parabola thereupon being integrated between the 3 central points $i_{n+1} - i_{n+3}$. The set of values so obtained results from displacing the computing templet by 2 increments in the direction of the positive time axis. The new subscripts so obtained then are $i_{n+2} - i_{n+6}$.

As the sole exception, the beginning segment is integrated within the first four points. This integration procedure ensures extreme accuracy by the overlapping junction of the compensating parabolae to the particular previous test points.

The total obtained can be displayed directly, but it can also be multipled by a factor taking into account special influences ascertained in particular patients as the normalized values. These normalized values for instance may be related to age, sex, hematocrit and similar values.

In lieu of the above described integration of area segments, the slope of a straight line passing through two or more test points obviously is obtained in numerical manner. The required mathematical algorithms for that purpose are known and again can be implemented by a microcomputer.

Furthermore, analog methods are known for ascertaining the slope of a curve and the area under the curve.

We claim:

1. In a method for obtaining measured test values from blood sedimentation corresponding to blood subsidence, by inserting a blood specimen in a transparent measuring chamber, removing erythrocyte aggregation present in the specimen, illuminating the specimen with light, and measuring the amount of light leaving the specimen over a given time, wherein:

(a) said specimen is inserted in a measuring chamber having upper (11) and lower (10) means movable relative to one another and the specimen comes in contact with said upper and lower means;

(b) erythrocyte aggregation present in said operation is counteracted by movement of said upper means relative to said lower means; and (c) the amount of light leaving said specimen during the aggregation process setting in again is photometrically measured after sudden stopping or after transition to a continuous minor residual shearing movement of said upper and lower means, and photometric signals are generated; the improvement comprising:

(d) ascertaining a syllectogram from said generated photometric signals;

(e) defining as the onset of the aggregation phase an extreme value of the syllectogram within a predetermined time interval of about 5 seconds following said sudden stopping of shearing or transition to a residual continuous shearing; and (f) ascertaining said test values at a predetermined time within approximately 2.5 seconds after onset of the blood aggregation from a slope of a test curve representing said syllectogram.

2. The method of claim 1, wherein said continuous minor residual shearing takes place in impulsive manner.

3. The method of claim 1, wherein said transition to continuous, minor residual shearing takes place gradually.

4. The method of claim 1, wherein a test curve representing the syllectogram is digitized.

5. The method of claim 4, wherein said digitizing takes place at a frequency of 20 hertz.

6. The method of claim 4, wherein the digitized test values are multiplied by a factor normalizing the incident light intensity.

7. The method of claim 4, wherein the digitized syllectogram is normalized within the predetermined testing time interval by subtracting the test value defining the onset of the aggregation phase.

8. The method of claim 7, wherein an area under the normalized, digitized syllectogram is determined by numerical integration during the predetermined time interval.

9. The method of claim 1, wherein testing takes place alternatively after suddenly stopping shearing and after transition to residual shearing.

10. The method of claim 1, wherein the step (f), said test values are ascertained from an average slope within a time interval of approximately 2.5 seconds after onset of the aggregation phase.

11. The method of claim 1, wherein in step (f), said test values are ascertained from an area under a test curve representing said syllectogram within a time interval of approximately 10 seconds beginning with the onset of the aggregation phase.

12. In an apparatus for rapidly ascertaining measured test values disclosing blood subsidence from a minimum amount of blood by measuring the natural aggregation rate of particles in liquid blood, comprising:

(a) means for illuminating and defining an optical axis;

(b) upper (11) and lower (10) means defining a transparent anti-aggregation chamber therebetween for being filled with a minimum amount of blood specimen, said blood specimen touching said upper and lower means and located along said optical axis;

(c) drive means for agitating said anti-aggregation chamber by way of slow motion of said upper means relative to said lower means and for separating said blood specimen;

(d) rapid shut-off means to retard or to stop said agitated chamber;

(e) photoelectric receiver means responsive to illumination leaving said anti-aggregation chamber; and (f) means for deriving electrical signals from said photoelectric receiver means after retarding or stopping said chamber over the whole aggregation time; the improvement comprising:

(g) an analyzing stage for providing a syllectogram from said electric signals and defining as the onset of the aggregation phase an extreme value of the syllectogram within a predetermined time interval of about 5 seconds following said sudden stopping of shearing or transition to a residual continuous shearing and ascertaining said test values at a predetermined time beginning within approximately 2.5 seconds after onset of blood aggregation from a slope of a test curve representing said syllectogram.

* * * * *